(12) United States Patent
Luotola et al.

(10) Patent No.: US 6,358,753 B1
(45) Date of Patent: Mar. 19, 2002

(54) METHOD OF COUPLING LIGANDS TO A SOLID PHASE IN ACIDIC SOLUTION AND ANIONIC SURFACTANT

(75) Inventors: Juhani Luotola, Espoo; Martti Malassu, Vantaa, both of (FI)

(73) Assignee: Orion-Yhtymä Oyj, Espoo (FI)

( * ) Notice: Subject to any disclaimer, the term of this patent is extended or adjusted under 35 U.S.C. 154(b) by 0 days.

(21) Appl. No.: 09/331,056

(22) PCT Filed: Dec. 10, 1997

(86) PCT No.: PCT/FI97/00774

§ 371 Date: Jun. 16, 1999

§ 102(e) Date: Jun. 16, 1999

(87) PCT Pub. No.: WO98/27429

PCT Pub. Date: Jun. 25, 1998

(30) Foreign Application Priority Data

Dec. 17, 1996 (FI) .................................. 965066

(51) Int. Cl.$^7$ ............................................ G01N 33/533
(52) U.S. Cl. .................. 436/518; 435/961; 436/523; 436/524; 436/528; 436/531; 436/533; 436/823; 427/532; 427/338; 427/402; 427/403; 427/412; 427/413; 427/810; 427/815; 427/866

(58) Field of Search .......................... 435/961; 436/518, 436/523, 524, 528, 531, 533; 427/823, 532, 338, 402, 403, 412, 413, 810, 815, 866

(56) References Cited

U.S. PATENT DOCUMENTS 4,703,018 A    10/1987    Craig et al.
5,401,634 A    3/1995    Milbrath

FOREIGN PATENT DOCUMENTS

EP    0 709 676 A2    5/1996

*Primary Examiner*—Bao-Thuy L. Nguyen
(74) *Attorney, Agent, or Firm*—Crowell & Moring LLP

(57) ABSTRACT

The present invention relates to a method for binding antibody or antigen molecules to solid phase. The reactive compound comprising an antibody or antigen molecule and a solide phase are formed by coupling a specific antibody or antigen molecule to a solid phase using a two-step reaction. The coupling is covalent, between the active groups of the solid phase and the antibody, a fragment thereof or the antigen molecule, in the presence of an anionic surfactant, after adding an alkaline/solution to raise the pH to the basic region.

24 Claims, 3 Drawing Sheets

METHOD OF COUPLING LIGANDS TO A SOLID PHASE IN ACIDIC SOLUTION AND ANIONIC SURFACTANT

The invention relates to a method for binding antibody or antigen molecules to solid phase. The reactive compound comprising an antibody or antigen molecule and solid phase is formed by coupling a specific antibody or antigen molecule to a solid phase using a two-step reaction. The final result is an antibody or antigen molecule complex which is covalently bound to the solid phase and is very active in immunological reactions. The bound antibody may be mono- or polyclonal, and a whole antibody or a part thereof. The present method enables carrying out immunological assays with very high specificity and sensitivity. The process of preparation is very simple compared to covalent coupling methods disclosed previously. The present invention can be exploited industrially in a test kit which includes a solid phase-biomolecule conjugate, i.e. a particle suspension or another solid phase, to which antibodies, their fragments, or antigens have been attached by the method according to the invention. The characteristics of the invention are defined in the claims.

There are prior known methods in which an antibody or antigen molecule is attached adsorptively or covalently to latex particles, or in which methods whole antibody molecules are modified (U.S. Pat. Nos. 5,095,097, 4,184,849, 4,210,723, 4,401,765, 4,480,042, 4,397,960 and 4,164,558 as well as European patent application 0 709 676 A2).

In the last-mentioned patent application (EP 0 709 676 A2) the pretreatment of a whole IgG-molecule in an acidic solution modifies the tertiary structure of the molecule, so that the attachment of a whole reformed IgG-molecule carried out after neutralization enables reduction of the disturbing factors in the connection of immunological assays. In addition, a zwitterionic or non-ionic surfactant is used in the method according to said patent application to enhance the covalent binding of the acid-treated and neutralized antibody on the surface of latex particles. In said patent application it is specifically mentioned that anionic or cationic surfactants are ineffective in enhancing the covalent binding of the antibody on the surface of the a latex particle. In the above mentioned patent application coupling chemistry is applied to specific core-shell particles, in which the actual covalent binding takes place between the methyl chloride, oxirane, carboxyaldehyde, tosyl, mesyl or n-acryloxysuccinimide groups of the outermost shell of a particle, or mixtures of such groups and the amino groups of the antibody molecule in the presence of a zwitterionic or non-ionic surfactant, or a mixture thereof. Said method is, however, suitable merely to the attachment of antibodies of IgG class, and thus it is not suitable for attaching e.g. antigen molecules, unlike the present method.

In quantitative and qualitative immunological assays the amount of either an antibody or an antigen is measured from biological fluids, secretions or tissue fluids (blood, serum, plasma, cerebrospinal fluid, pleural fluid, ascites fluid, pus, wound secretion, urine, sputum, faeces, pharyngeal sample, etc.). Tests can be either direct, non-direct or inhibitory. In immunological reactions the antibody binds to an antigen structure specific to said antibody. Either the antibody or the antigen can be bound to a specific signal substance (label). Labels include polymeric particles (also colored and magnetic). The antibody or antigen molecules can also be attached on the surface of a solid phase of another type (e.g. a microtitre plate or a test tube or a cuvette carrying active binding groups on its surface). In quantitative assays an analysis equipment is often used, the principle of which is the optical measurement of the sample (absorbance, extinction, nephelometry, reflectance, fluorescence, phosforescence, etc.).

In the present method an antibody (a whole molecule or its fragment) or, alternatively, an antigen molecule (including e.g. haptens, lectins or chemical compounds) is attached in two steps on the surface of a copolymeric styrenvinylbenzylchloride (S/VBC) particle in the presence of an anionic surfactant, thereby achieving as an end product a covalent particle-antibody complex or, alternatively, a covalent particle-antigen complex. Polymer particles can be homopolymeric or copolymeric or they can be core-shell particles. The size range of the particles is typically from 10 nm to 10000 nm. As particle materials, besides S/VBC, polystyren, polyvinylnaphthalene, polyvinylcarbazole, polyvinyltoluene, polyvinylbutylstyren, polyvinylbenzene, polyvinylchlioride, and mixtures thereof come into question. Besides particles, the solid phase can also be e.g. a microtitre plate, a test tube, an assay cuvette, immunochromatography material, a filter, a test strip or gold colloid.

In the present method when the antibody, a fragment thereof, or the antigen is attached to the solid phase, their structure is modified to be advantageous for the coupling in statu nascendi and for an immunological reaction. The coupling is covalent, when it takes place between the active groups of the solid phase and the antibody, a fragment thereof or the antigen molecule, in the presence of an anionic surfactant.

As mentioned above, particles prepared of raw materials other than S/VBC come into question. These raw materials are selected e.g. from polystyrene, polyvinylnapthalene, polyvinylcarbazole, polyvinyltoluene, polyvinylbutylstyrene, polyvinylbenzene and polyvinylchloride, and their mixtures, as well as colloidal gold. The present coupling method differs from the prior disclosed (EP 0 709 676 A2) e.g. in that the antibody molecule to be coupled can be a whole molecule or a fragment thereof, and also an antigen molecule. In addition, the method is very rapid to carry out as it does not require separate steps or coupling reagents, which even as such may denature the biomolecules to be coupled with e.g. intra- and intermolecular cross linkages (e.g. carbodiimide linkages). The method of the invention enables also a very long storage time of the prepared reagent (i.e. solid phase-biomolecule conjugate) in both soluble and lyophilized form.

Coupling takes place at the first step very rapidly substantially via hydrophobic interactions (hydrogen bonds, van der Waals forces) and at the immediately following second step covalently, whereby the methyl chloride groups react with primary or secondary amino groups of the antibody molecules (a whole molecule or a fragment thereof) or the antigen molecules (substitution reaction). It is also possible that methyl chloride groups react with some other groups. Covalent binding is a fairly slow event, and enhancement thereof requires basic pH (8 to 11, preferably pH 9.0). Except methyl chloride groups, also epoxy, aldehyde, tosyl, mesyl or n-hydroxysuccinimide groups, or mixtures thereof, can act as covalently binding groups of the solid phase, whereby the conditions of the actual covalent reaction step (step 2) have been optimized for said reaction chemistry.

In the coupling procedure the S/VBC particles are transferred by dialysis to a dilute acid or a buffer solution, preferably to 5 mM HCl (pH 2 to 6, preferably 2.5), whereto an anionic surfactant, preferably the surfactant polyoxy-1, 2-ethane diyl-α-nonylphenyl-o-hydroxy-phosphate Rhodafac-RE610), is added under stirring, to achieve a surfactant concentration of 0.01 to 0.1%, preferably 0.025%, at the final coupling step, depending on the antibody or antigen used. The antibody or antigen, preferably as a 0.9% solution in NaCl is added under vigorous stirring into the particle suspension in 5 mM HCl, to achieve a particle concentration of about 0.5 to 10%, preferably 2% at the coupling step. The concentration of the antibody or antigen at the coupling step is 0.01 to 1%, preferably 0.01 to 0.2%, depending on the antibody and the antigen used. The ratio of the antibody or the antigen to the dry weight of the S/VBC particles is 0.001 to 1.0, most preferably 0.1 to 0.3.

The mixture of the antibody or antigen and the SNVBC particles is incubated for 1 to 60 minutes, preferably for 10 to 20 minutes at 4° C. to 50° C., preferably at 20 ° C. During the incubation an effective, essentially adsorptive attachment of the antibody or antigen onto the surface of the particle takes place in the presence of an anionic surfactant (the first step of the coupling reaction). Then a basic buffer solution, preferably 0.1 M borate buffer, pH 9.0 is added, so as to double the volume, and to achieve a particle concentration of 1%. The mixture is incubated for 16 to 24 hours at 4° C. to 50° C., most preferably at 20° C. stirring continuously, whereby the actual covalent coupling essentially takes place (the second step of the coupling reaction).

The present coupling method differs from the earlier disclosed methods (EP 0 709 676 A2) e.g. in that the coupling reaction (the first step) takes place direct in acidic pH in the presence of an anionic surfactant (in the earlier patent applications in the presence of a cationic surfactant), whereafter the covalent step of the coupling reaction (the second step) is carried out without a separate neutralizing step (in the earlier patent applications there is a separate neutralizing step) in basic pH.

In the following the invention is illustrated in detail by examples. The examples describe specific applications of the above indicated coupling method and are not intended to restrict the invention.

EXAMPLE 1

Figure 1:
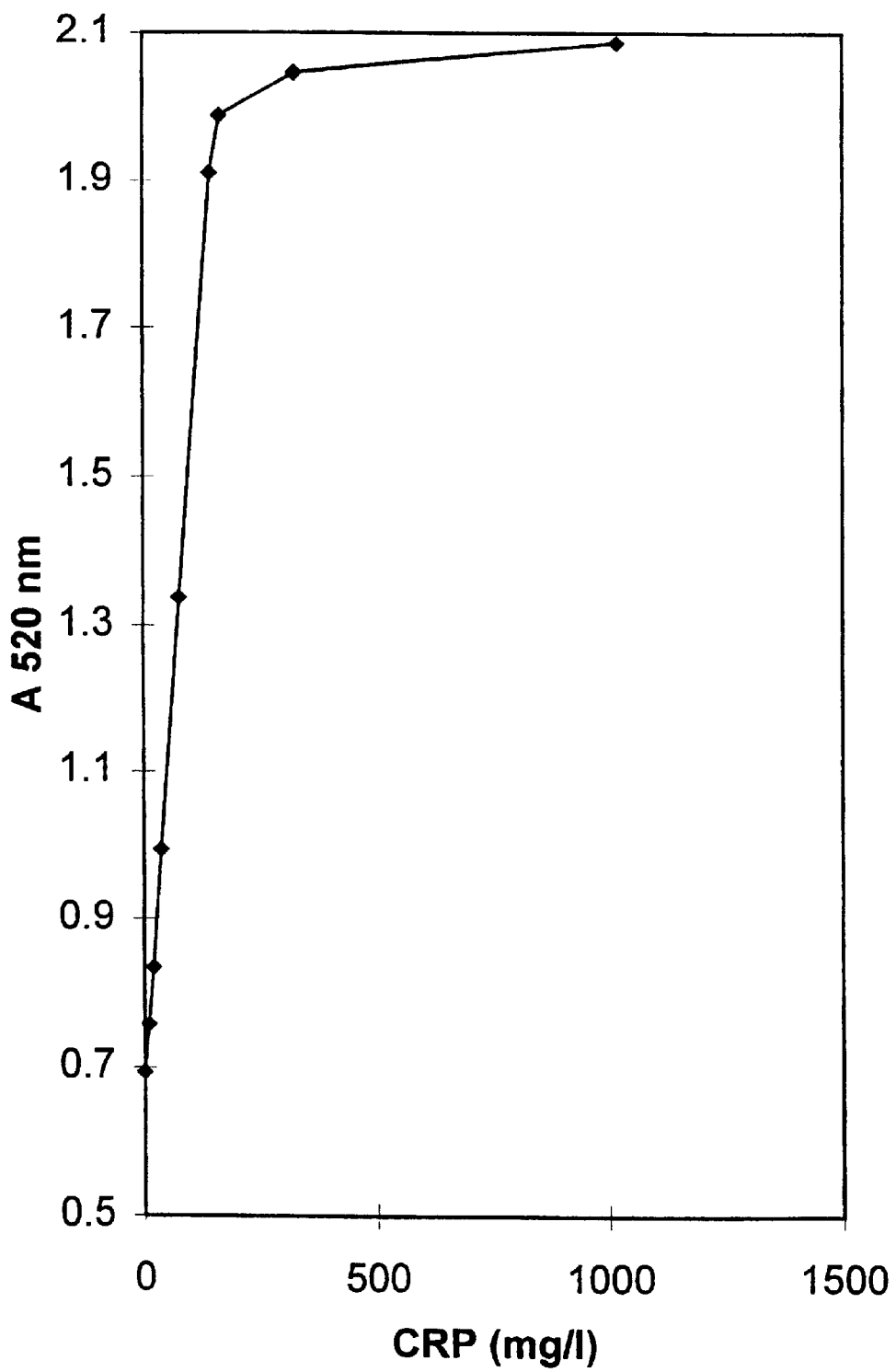
FIG. 1 Assay of C-reactive protein (CRP). A typical reaction curve obtained using a reagent prepared according to the invention.

The C-reactive protein (CRP) is a generally accepted indicator of inflammatory reactions, which is supposed to be determined from a whole blood sample or a serum sample of a patient. CRP assay is often carried out using an analysis device with a principle of optical measurement (absorbance, extinction, nephelometry, reflectance, fluorescence, phosforescence, etc.) of the sample. To determine the CRP concentration polymeric particles are prepared which are coated with a sheep anti-human-CRP antibody (F(ab')$_2$ fragment). The procedure according to the invention is as follows: to one ml of the particle suspension of S/VBC (9% suspension in 5 mM HCl, particle size 90 nm) 0.33 ml of 0.9% Rhodafac-RE610 solution in NaCl is added. The mixture is stirred at room temperature for 15 minutes. To the mixture 1.82 mg of anti-human-CRP-F(ab')$_2$-antibody per 10 mg of particle dry weight is added, diluted with 0.9% NaCl, to obtain a particle concentration of 2% in the suspension. The mixture is stirred at 20° C. for 15 minutes, while controlling the pH. A suitable pH range is 2.5 to 3.0. To the mixture 0.1 M borate buffer, pH 9.0, is added to double its volume. pH should be 9.0. The mixture is stirred for 18 hours at 20° C. The non-reactive active groups on the surface of the particles are blocked with 30 mM glycine buffer including 6% of BSA (Bovine Serum Albumin) and 0.1% NaN$_3$, pH 8.7 so that the BSA-concentration will be 0.2%. The mixture is shaken for 16 hours at 20° C. The coated particles are washed by centrifugation or diafiltration in a washing buffer solution (30 mM glycine, 0.1% BSA, 0.1% NaN$_3$, pH 8.7), whereafter they are transferred to a storage buffer solution (30 mM glycine, 0.1% BSA, 5% sucrose, 0.1% NaN$_3$, pH 8.7). The particle suspension is sonicated until the particle size is under 110 nm and the suspension is in monodisperse form. The final particle concentration is adjusted according to the application in the storage buffer solution to be 1 to 4%. A typical reaction curve achieved using the reagent so obtained is given in FIG. 1.

EXAMPLE 2

Figure 2:
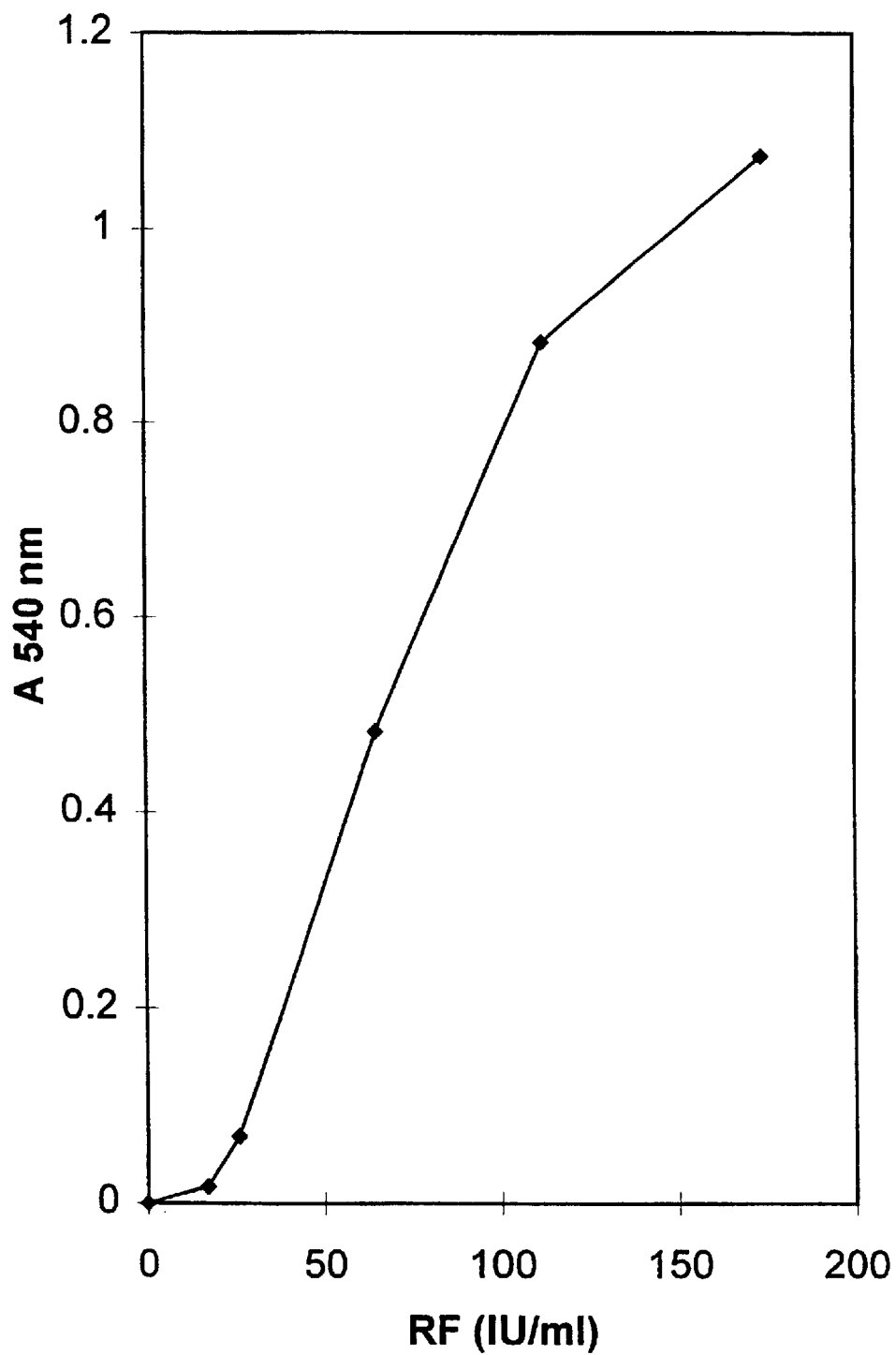
FIG. 2 Assay of rheumatoid factor (RF). A typical reaction curve obtained using a reagent prepared according to the invention.

Determination of the rheumatoid factor (RF) is very important in the diagnosis of various rheumatoid diseases. The rheumatoid factor is an autoantibody of the immunoglobulin class M formed by a human being, directed against an IgG of his own. A reaction between RF and the own structures (IgG) of the human being releases a disease, which in its common form is rheumatoid arthritis. Determination of RF can be carried out as described in the previous example, directly from a whole blood sample or from serum. In this test the specific labeling particles have been coated with human immunoglobulin G molecules. The actual coupling reaction is carried out as described in the previous Example, but the anti-human-CRP-antibody CRP-antibody (F(ab')$_2$ fragment) is replaced in the coupling reaction by a human IgG molecule. A typical reaction curve achieved using the reagent obtained is given in FIG. 2.

EXAMPLE 3

Figure 3:
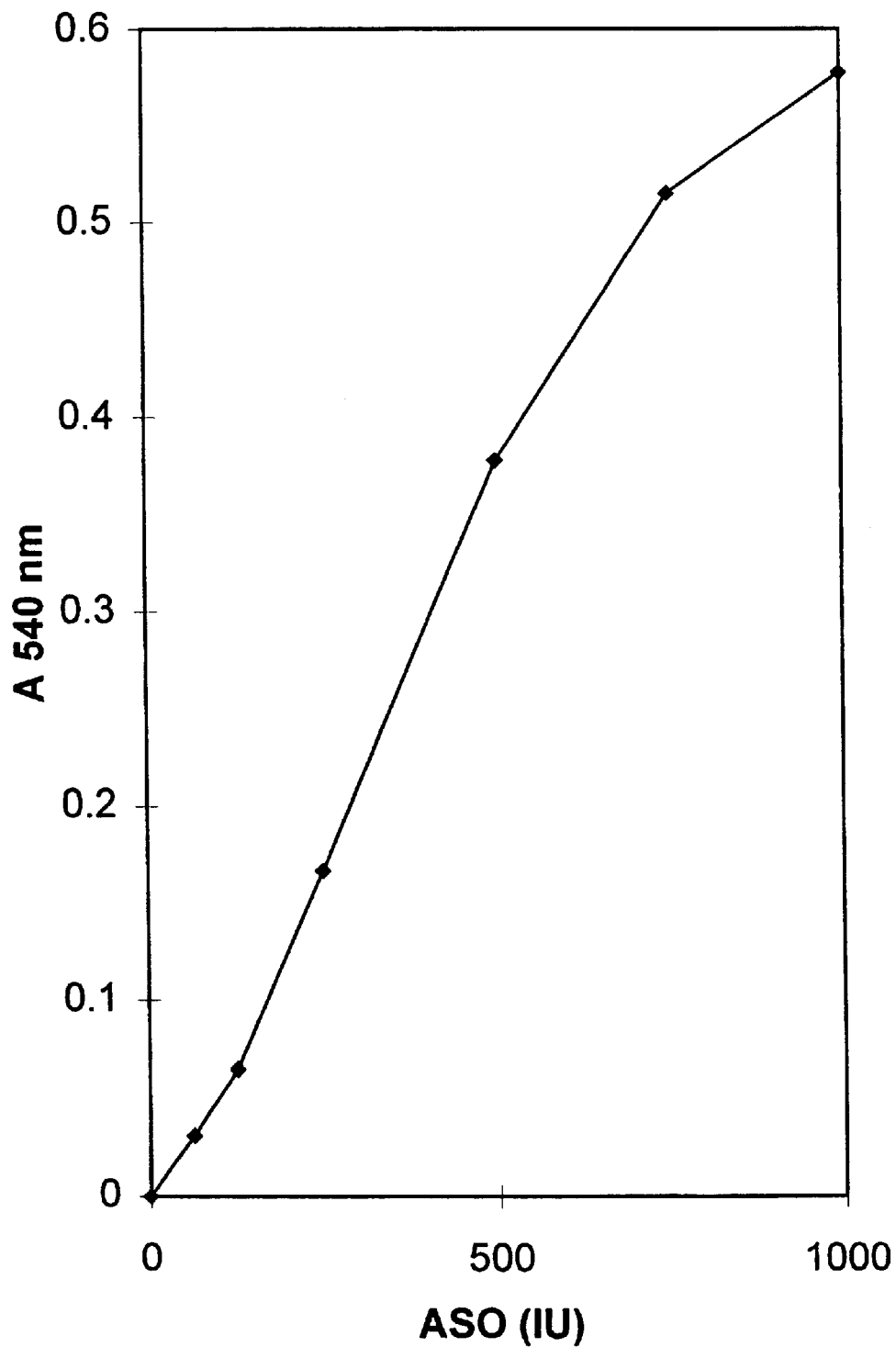
FIG. 3 Assay of streptolysin O. A typical reaction curve obtained using a reagent prepared according to the invention.

Streptococci of group A produce to their environment various compounds, which can be detected. Some of these extracellular products are toxins. One of such toxins is streptolysin O. An infection by streptococci of group A generates antibodies in a human being. An antibody test, which in most cases is carried out to detect group A streptococcal infection, is an ASO test (anti-streptolysin O). About 80% of the patients having an acute group A streptococcal pharyngitis generate antibodies against streptolysin O. In addition, the ASO determination is recommended in the detection of rheumatic fever and glomerulonephritis. Using the two-step coupling method of the invention streptolysin O antigen (SLO) can be attached on the surface of the SNVBC particles. So it is possible to determine antibodies against SLO in the patient samples (ASO test). The coupling is carried out as described above to the antibodies or their fragments, i.e. in two steps. A typical reaction curve achieved using the reagent obtained is given in FIG. 3.

What is claimed is:

1. A method for covalent coupling of an antibody molecule, a fragment thereof, or an antigen molecule to a solid phase, comprising:

a) bringing an antibody, a fragment thereof, or an antigen, in the presence of an anionic surfactant, in to contact with a solid phase which is present in an acidic pH solution to attach said antibody, said fragment thereof, or said antigen to the solid phase to form a mixture, and b) adding a basic pH solution to the mixture obtained at step a), to change the pH to be basic in order to form covalent bonds between primary or secondary amino groups of the antibody, the fragment thereof, or the antigen and functional groups of the solid phase.

2. The method of claim 1, wherein the acidic pH solution is hydrochloric acid.

3. The method of claim 2, wherein the acidic pH solution is 5 mM hydrochloric acid at a pH of 2–4.

4. The method of claim 1, wherein the basic pH solution is a borate buffer.

5. The of claim 4, wherein the basic pH solution is 0.1 M borate buffer at a pH of 9.0.

6. The method of claim 1, wherein the anionic surfactant is polyoxy-1,2-ethane-diyl-α-nonylphenyl-o-hydroxy-phosphate surfactant at a concentration of 0.1 to 0.01%.

7. The method of claim 1, wherein the functional groups of the solid phase are selected from the group consisting of chloromethyl, epoxy, aldehyde, tosyl, mesyl, n-hydroxysuccinimide groups, and mixtures thereof.

8. The method of claim 7, wherein the functional group of the solid phase is chloromethyl.

9. The method of claim 1, wherein step a) takes 5 to 60 minutes.

10. The method of claim 9, wherein step a) takes 15 minutes.

11. The method of claim 1, wherein step b) starts immediately after step a), and takes 1 to 24 hours.

12. The method of claim 11, wherein step b) takes 18 hours.

13. The method of claim 1, wherein the solid phase is a polymer particle, a microtitre plate, a test tube, an analysis cuvette, immunochromatography material, a filter, a test strip or gold colloid; preferably a polymer particle.

14. The method of claim 13, wherein the polymer particles have been formed of a homopolymer or a copolymer or are core-shell particles.

15. The method of claim 14, wherein structural components of the polymer particles are selected from the group consisting of polystyrene, polyvinylnapthalene, polyvinylcarbazol, polyvinyltoluene, polyvinylbutylstyrene, polyvinylbenzene, polyvinyl chloride, and mixtures thereof.

16. The method of claim 15, wherein a structural component of the polymer particles is a copolymer of polystyrene and polyvinyl chloride.

17. The method of claim 16, wherein the polymer particles are 10 to 10000 nm in size.

18. The method of claim 17, wherein the polymer particles are 90 nm in size.

19. The method of claim 15, wherein the polymer particles are 10 nm to 10000 nm in size.

20. The method of claim 19, wherein the polymer particles are 90 nm in size.

21. A solid phase-biomolecule conjugate, comprising a solid phase wherein antibody molecules, a fragment thereof, or antigen molecules have been covalently attached using the method of claim 1.

22. The solid phase-biomolecule conjugate of claim 21, comprising a F(ab')$_2$ fragment of a sheep anti-human-CRP-antibody coupled to styrenvinyl-benzylchloride polymer particles.

23. A diagnostic test kit which comprises a solid phase-biomolecule conjugate of claim 22.

24. A diagnostic test kit which comprises a solid phase-biomolecule conjugate of claim 21.

* * * * *